United States Patent [19]

von Hagens

[11] 4,320,157
[45] Mar. 16, 1982

[54] METHOD FOR PRESERVING LARGE SECTIONS OF BIOLOGICAL TISSUE WITH POLYMERS

[76] Inventor: Gunther von Hagens, Jahnstrasse 8, Heidelberg, Fed. Rep. of Germany, D-6900

[21] Appl. No.: 176,350

[22] Filed: Aug. 8, 1980

[51] Int. Cl.³ .................... A47G 1/12; B29D 3/00
[52] U.S. Cl. ............................... 428/13; 264/279.1; 427/4; 434/296; 156/57
[58] Field of Search .................. 264/299, 102, 271; 35/20; 427/4; 428/13

[56] References Cited

U.S. PATENT DOCUMENTS 4,205,059  5/1980  von Hagens ..................... 427/4

OTHER PUBLICATIONS

Dupart Information Bulletin, No. X–28C.
Plastics World, Aug. 1947.

Primary Examiner—Sam Silverberg
Attorney, Agent, or Firm—Michael Ebert

[57] ABSTRACT

A method for preserving a large section of biological tissue with a curable polymer such as an acrylic resin by impregnating the large section with the polymer and pressing the impregnated large section between flat plates. These plates are further separated near their edges by an elastomeric material, thereby providing a flat cell in which the opposing cut surfaces of the impregnated large section abut the inner surfaces of the cell plates. Thereafter the cell is filled up with uncured polymer. The polymer is then cured, the plates moving toward each other due to the polymer shrinkage during curing. Finally, the plates are removed. The resulting plastinated sheet is a permanently-preserved large section of biological tissue whose tissue water is completely replaced by a cured polymer, the sheet having a uniform thickness and smooth, even surfaces.

19 Claims, 1 Drawing Figure

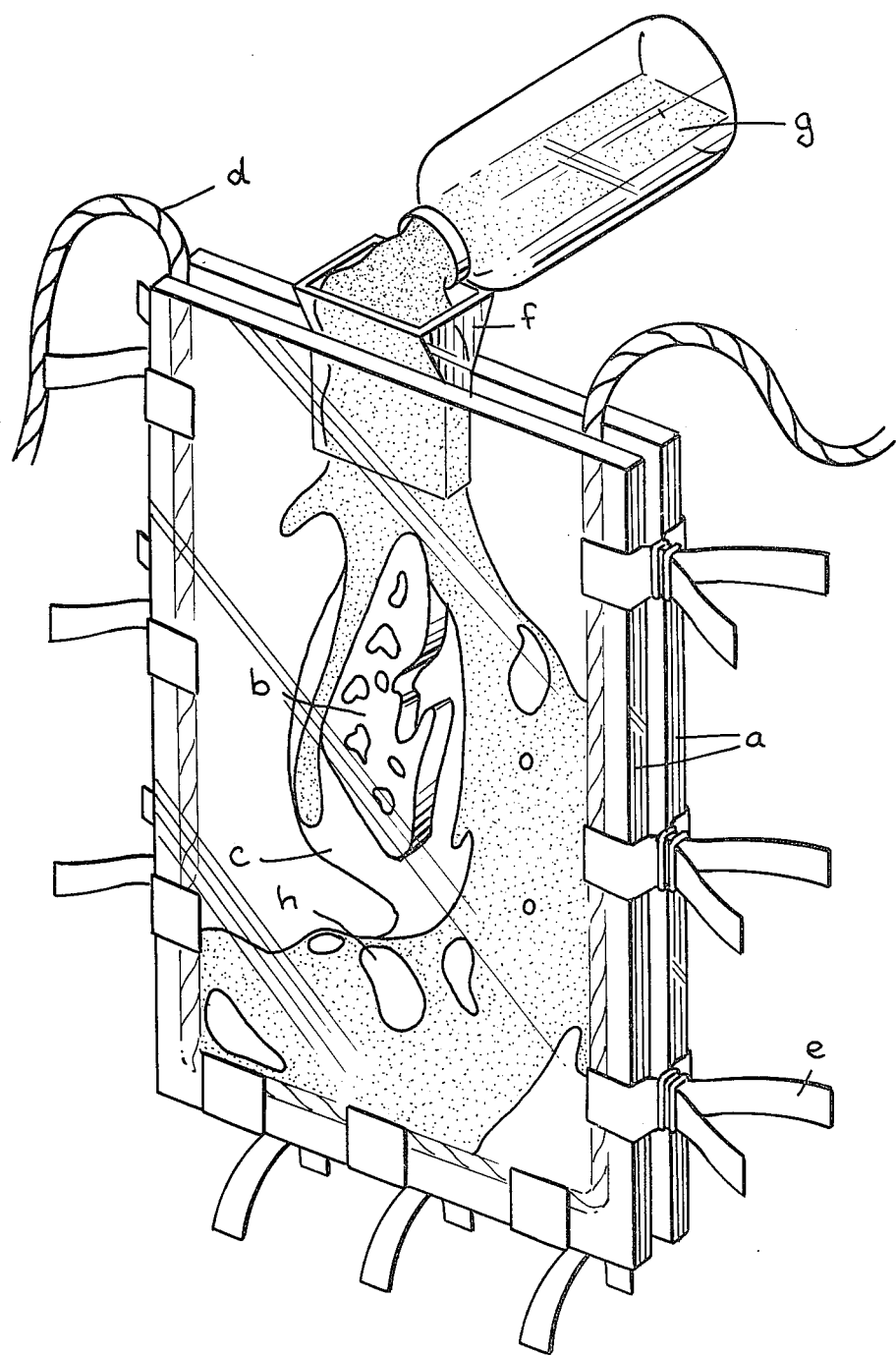

METHOD FOR PRESERVING LARGE SECTIONS OF BIOLOGICAL TISSUE WITH POLYMERS

BACKGROUND OF INVENTION

This invention relates generally to the preservation of large sections of biological tissues, and more particularly to a method which converts such a section, e.g. cross section of a rabbit, into a plastinated sheet. In a method in accordance with the invention, the tissue water of the large section is replaced by a polymer, thereby preserving the large section of biological tissue permanently.

Large sections of biological tissue, especially sections of whole organs and bodies of animal or human origin are often required for teaching and scientific purposes in the fields of anatomy, pathology, forensic medicine, biology and the like.

Large sections have heretofore been preserved by the following methods:

(1) Gelatine—and Paper method: With gelatine preservation, impregnated sections are glued on plates of acrylic resin (Improved Plastic Embedding of Wet Biological Specimens, by Simmons, E. M. et al. in MEDICAL AND BIOLOGICAL ILLUSTRATIONS, 18, 260–262) or on paper (Rapid Paper Sections of Solid Organs, by Whimster, W. F., in Human Pathology 1, 1, 1970).

(2) Embedment: The sections are embedded in blocks of plastic. To this end, a bottom, a specimen and a top layer must be poured (A Simple Method for Embedding Anatomical Specimens, by Grimsrud, O. K., and Dugstad, G., NEURORADIOLOGY 10 143–145, 1975; Preparation of Plastic Mounted Brain Specimens, by Deonar, V., NEURORADIOLOGY 4, 197–201, 1972).

(3) Polymer impregnation: A method of impregnating large sections with uncured polymers with subsequent curing between separating foils is described in "Impregnation of Soft Biological Specimens with Thermosetting Resins and Elastomers," by v. Hagens, G., THE ANATOMICAL RECORD 194, 247,256, 1979.

These known methods as well as the preserved products attained thereby suffer from serious disadvantages, as will now be explained:

(1) Gelatine—and Paper method: The preserved large section is not resistant to scratches (gelatine surface) or to mechanical stress (paper as supporting medium). Because of the acrylic sheet functioning as a supporting medium, the preserved large section is considerably thicker than the tissue section.

(2) Embedment: Due to the bottom and the top layer of cured resin, the thickness of the resulting block is considerably thicker than the large section itself. Details of the specimen cannot be viewed directly with the aid of a magnifier. Because it is necessary to pour three layers of resin at different times and the surface of the cured block has to be ground and polished, this method is quite time-consuming and costly.

(3) Polymer impregnation: Because of the firmness of the polymer material and the minimal thickness of the resulting sections, this method appears to be quite advanced. However, this technique for preserving a large section lacks uniform thickness and surfaces which are even or polished. Moreover, it is very difficult to remove air bubbles in the vicinity of the tissue section.

It is also known from the literature (POLYMER PROCESSES, Vol. X, by Schildknecht, C. E., Interscience Publishers Inc., New York, p. 35, 1956) that acrylic sheets can be made by casting uncured polymer (catalyzed prepolymer or monomer) in a cell defined by glass plates. The glass plates are separated from each other along their outer edges by an elastomeric material in order to prevent leakage of the uncured polymer. These plates are subjected to a constant pressure which causes the plates to move toward each other in the course of polymer shrinkage during polymerization. The resulting transparent sheets of organic glass exhibit a uniform thickness and surfaces which are even and polished. These sheet properties are also desirable in the context of a plastinated sheet preserving a large section of biological tissue.

SUMMARY OF INVENTION

Accordingly, the main object of this invention is to provide a method for converting a large section of biological tissue into a plastinated sheet having smooth surfaces and a uniform thickness.

A significant aspect of the invention is that it combines the known technology of preserving large sections with the otherwise unrelated art of casting sheets of organic glass to produce a unique plastinated sheet.

We shall now summarize the major advantages to be gained by sheet-plastination.

The method makes it possible, without difficulty, to preserve a very large section (e.g., from a cow), because during the curing step the large section is pressed between plates acting as a supporting medium. Since the closed cell with the impregnated tissue section therein can be tilted, this causes air bubbles in the vicinity of the section to rise and disappear. The method, if performed by a skilled person, may be carried out quickly. Moreover, the method is inexpensive as regards consumption of polymer and biological material.

As regards the product: The surface of the plastinated sheet is smooth, thereby obviating the need for time-consuming polishing operations. A plastinated sheet can be made as thin as 0.2 mm. Such very thin plastinated sheets afford optimum light transmittance. The plastinated sheet is of uniform thickness. The structure of the plastinated sheet can be viewed and directly marked. As a consequence, explanatory indicia can be inscribed in the immediate vicinity of the structures of interest. Thus the invention affords a highly valuable aid for teaching and demonstration purposes in morphology.

OUTLINE OF FIGURE

For a better understanding of the invention as well as other objects and further features thereof, reference is made to the following detailed description to be read in conjunction with the accompanying drawing, whose single FIGURE illustrates a cell adapted to carry out a method in accordance with the invention to produce a plastinated sheet.

DESCRIPTION OF INVENTION

The terminology used herein is to be construed in the light of the following definitions:

"Large section" is intended to mean one or several sections of biological tissue, especially of human or animal tissue, as obtainable with a rotary slicing machine or a saw. Large sections are usually obtained from whole organs, bodies or parts thereof. The thickness of large sections ranges between 0.2 mm and 5 mm, their maximal thickness and size not being limited. It is apparent that large sections in this sense are quite different from tissue sections as known from histology which are obtained with the aid of a microtome with a thickness between 1μ and 50μ and which are preserved permanently between glass plates.

"Impregnated section" or impregnated large section is intended to mean a large section whose tissue water is completely removed by an uncured, partially cured (i.e., gelated) or cured polymer. Because only a minimal amount of additional polymer is situated around the impregnated section, its size is about equal to that of the large section in its fresh state.

"Plastinated sheet" is intended to mean a large section impregnated with a cured polymer, which is surrounded by additional cured polymer almost exclusively around its outer periphery. The surface of the plastinated sheet is smooth, its thickness uniform and about equal to that of the large section before treatment.

"Uncured polymer" is intended to mean a fluid precursor composition capable of being polymerized into a solid synthetic resin or firm elastomer. The uncured polymer is taken from the class of thermosets and elastomers. It experiences a certain amount of shrinkage during polymerization, ranging from less than 1% to more than 20% by volume. More specifically, compounds taken from the following classes of polymers have been used successfully: Acrylic resins (e.g., methylmethacrylate), allyl compounds (e.g., copolymers of allyl diglycol carbonate), epoxy resins, polyester resins, polyurethanes and silicone rubber. However, the invention encompasses polymers which are uncured in a fluid state and which are capable of being cured into a solid synthetic resin or firm elastomer.

"Partially cured polymer" is intended to mean a fluid precursor composition as defined in the foregoing paragraph which is polymerized to its gelated state.

"Cured polymer" is intended to mean a cured thermoset or elastomer of the type described in the foregoing paragraphs. Optically clear polymers are preferable for this purpose.

"Specimen" is intended to mean whole organs, bodies or parts thereof, including extremities and virtually all kinds of biological material whose conversion into plastinated sheets is desirable.

"Last intermedium" is intended to mean an organic solvent such as xylene, acetone, methylene chloride or propylene oxide which is miscible with the uncured polymer used for impregnation and which serves as an immersion bath after the dehydration procedure and before impregnation with the uncured polymer.

From the standpoint of processing, the different procedures entailed in a method in accordance with the invention shall be classified for convenience into three distinct stages—namely: (I) pretreatment of large section, (II) impregnation with polymers, and (III) casting the plastinated sheets. These stages shall now be set forth in greater detail.

Stage I—Pretreatment of large sections

Pretreatment of large sections includes cutting, fixation, preservation of color and/or staining and dehydration. Cutting of large sections: Specimens which contain solid substances like bone or horn are cut into large sections in their frozen state, preferably at a temperature below $-20°$ C. Specimens consisting uniformly of soft, putrifiable tissue (e.g., a lung section) are preferably cut by means of a rotary slicing machine in their frozen and/or fixed state.

Fixation: Either the specimen or the large sections obtained therefrom are fixed with known fixatives like formaldehyde or glutaraldehyde. Preservation of color and/or staining: The natural color can be preserved by known techniques such as by the addition of sodium nitrite and ascorbic acid to the fixing solution. For staining, known staining techniques for organic material may be used for this purpose. It has been proven useful to stain with techniques known from paraffin-histology.

Dehydration: Because almost all polymers which are useful for this invention are not miscible with water, the tissue water of the large sections must be exchanged with an intermedium that is compatible or at best fully miscible with the uncured polymer that is used. Dehydration by sequential immersion in e.g. five aqueous ethanol solutions ranging in concentration from 50 to 96% and final immersion in acetone as well known from paraffin-technology has proven to be very suitable. At the conclusion of pretreatment, the large section is imbued with an organic solvent, named "last intermedium" which is substantially free of water, which has preferably a high vapor pressure such as acetone or methylene chloride, and is miscible with the uncured polymer that is used.

Stage II—Impregnation with uncured polymer

Preserved and dehydrated large sections which have been prepared by the procedures in Stage I are immersed into a solution of uncured polymer. In the rare case where the uncured polymer used is miscible with water (e.g., hydroxaethylmethacrylate), the large section can be transferred from water directly into the water compatible polymer. Impregnation of the large section is achieved either by simple immersion in the uncured polymer and thus impregnated by diffusion or, especially if the large section's thickness exceeds 0.5 mm, by forced impregnation. To achieve this, as last intermedium an organic solvent has to be used which is characterized by a high vapor pressure like acetone or methylene chloride. The large section, imbued with this kind of last intermedium, is then immersed in a vat containing the uncured polymer which is ready for curing (e.g., by addition of a hardener) and placed into a vacuum chamber which is evacuated gradually. The last intermedium is now continuously removed in its gaseous state by a vacuum pump and gradually replaced by the still uncured polymer that is used. The infiltration of the polymer into the tissue is facilitated by the presence of the last intermedium because of its properties as a solvent.

This technique of impregnating biological specimen with curable polymers is known and described in greater detail in my U.S. Pat. No. 4,205,059, whose entire disclosure is incorporated herein by reference. Once the large section is impregnated, it is kept in the uncured polymer for processing in stage III or put between separating foils and cured until the polymer is gelated or until it is fully cured. At the end of the impregnation procedure, the large section is uniformly impregnated with an uncured, partially or fully cured polymer.

Stage III—Casting plastinated sheets

This stage is the crux of my invention. The critical procedure of this stage is illustrated in the drawing, where it will be seen that two plates (a), preferably in the form of clean, toughened glass plates of about the same size, are employed. If necessary, these plates are treated with a release agent. A selected uncured polymer which is de-aired is poured as a thin layer (c) in the center of one of the glass plates. Formation of air bubbles should be avoided.

The large section which has been prepared by the procedures in stages I and II, impregnated with cured, partially cured (e.g., jelled) or uncured polymer, is now placed onto the poured layer of uncured polymer. The entrapment of air bubbles must be avoided. Thereafter, a flexible gasket (d) of elastomeric material, preferably made out of especially graded polyvinylchloride and with a thickness about equal to that of the impregnated section, is now placed on the glass plate.

For an inexperienced operator, it may be helpful to hold the gasket in its position with the aid of a very thin polyamid-thread which is held in turn with pressure-sensitive tape on the reverse side of the glass plate. Thereafter, the impregnated large section is covered with an additional thin layer of uncured polymer.

The first glass plate (a) with the impregnated large section (b), the flexible gasket (d) and the poured polymer (c) is now covered by the second glass plate (a). During this procedure, one must be careful to avoid the entrapment of air bubbles above the impregnated large section.

As the next step in this procedure, the two glass plates (a) are pressed together by specially designed clamps (e) which hold the impregnated large section and the flexible gasket in position, thereby defining a flat cell in which the opposing cut surfaces of the impregnated large section (b) abut the inner surfaces of the two glass plates (a). When pressing plates (a) together, polymer (c) is squeezed out into the region surrounding the section.

Now, a specially designed funnel (f) is inserted into the upper slot of this flat cell. The flat cell is brought to an upright position, as shown in the drawing, and additional polymer (g) is poured into the cell to merge therein with the polymer (c) previously introduced to fill the cell completely. Air bubbles (h) are allowed to rise. To permit manipulation of the cell in order to direct the air bubbles away from the section therein, both ends of the flexible gasket are fused together with a soldering tool and squeezed fully between the glass plates to close the cell and thereby prevent leakage of the polymer therefrom during manipulation. Polymerization of the uncured polymer can now be effected. This may be done, depending upon the type of uncured polymer used, by means of elevated temperature, ultraviolet radiation or other known methods.

During polymerization, the two plates move towards each other, this movement being facilitated by the elasticity of the materials involved; i.e., the flexible gasket, the glass plates and the impregnated large section. After curing, the clamps are removed and the glass plates of the flat cell are taken apart. The plastinated sheet so produced is now cut into a convenient shape and, if desired, inscribed for educational or other purposes.

The casting of plastinated sheets directly on glass plates with polymers which do not have a distinct gelating phase, e.g., methacrylates, causes the plastinated sheet to have glass-like surfaces. Casting of plastinated sheets directly on glass plates with polymers which exhibit a distinct gelating phase, combined with substantial shrinkage during final curing in hampered by the formation of boundary lines on the surface of the cured plastinated sheet. Boundary lines will especially appear if there is rapid curing. These lines usually arise in the direct vicinity and around the impregnated large section and in the surrounding cast polymer region.

In general, there are two ways to prevent the formation of boundary lines. If casting is done directly on glass plates, it is advisable to remove the plastinated sheet from the plates when still in its partially cured state in order to hang it up or wrap it up in flannel for final curing. Secondly, the use of separating foils will prevent the formation of boundary lines. The separating foil may be either sealed upon the glass plate or just put on the glass plate. In the latter case, a much thicker foil (e.g. 350μ) is most useful. A preferred material for a separating foil is PETP (polyethylene terephthalate). The term foil as used herein is intended to cover thin plastic film sheets such as those made of Mylar.

The use of separating foils as coverage for the glass plates gives rise to certain adverse effects: While the use of separating foils is of advantage to prevent the formation of air bubbles because the foil can be bent if the impregnated section is covered therewith, the surface of the plastinated sheet is not as smooth when coming from foils rather than directly from the glass plates.

In casting plastinated sheets, bubble formation must be avoided. There are several ways of preventing bubbles. For example, if a section impregnated with cured polymer is used for casting a plastinated sheet, it is advisable to impregnate this cured large section with the setup of uncured polymer for casting the plastinated sheet. This procedure will fill up all pores on the surface of the cured large section with the uncured polymer and thereby prevent the formation of air bubbles which otherwise may expand and appear when the temperature of the polymer rises during curing.

The glass plates can be wrapped with very thin foils (thickness, e.g. 12μ) in order to prevent adhesion of polymers to glass and covered with an additional separating foil. It is also possible to cover the glass plates with a foil having adhesive properties on its outer face. Once the polymer of the plastinated sheet is cured, it adheres permanently to these foils. This modification of the method is especially useful should delicate silicone-rubber be used for casting plastinated sheets.

In those instances where a large section is to be formed—e.g., whole sections of a cow—it may be advisable in order to stabilize the section during processing, to cut or saw the large section to be impregnated in a slice which is quite thick; e.g., 8 mm. After impregnation and curing of this large section, it can be ground with emery paper to a thickness of, e.g., 2.5 mm. Thereafter, casting is carried out with this ground-down impregnated large section.

While the above description includes many specific details, these should not be construed as limitations on the scope of the invention, but rather as preferred embodiments thereof. Many other modifications in the procedure are possible. For example, the impregnation of large sections with uncured polymer may be facilitated by vibration. If a plastinated sheet is of reduced quality, as a result, for example, of bubble formation taking place during curing, it can be excised, possibly reground and again casted. It is also understood that several steps described herein can be omitted or performed in another sequence. For example, the staining of the large section, if desired, can be carried out at various stages or it may be entirely omitted.

I claim:

1. A method of converting a cut section of biological tissue into an examinable plastinated sheet in which the tissue is permanently preserved, said method comprising the steps of:

A pretreating the cut section to render it suitable for impregnation;

B impregnating the pretreated section with a fluid precursor composition;

C compressing the impregnated section between parallel plates having smooth inner surfaces whereby the opposing cut surfaces of the section abut the inner surfaces of the plates, the plates being separated by a compressible gasket to define a flat cell having a vacant region therein adjacent the periphery of the section;

D filling the flat cell with a fluid precursor composition which occupies said vacant region;

E curing the fluid precursor composition in said cell in a manner avoiding the formation of boundary lines, the resultant shrinkage causing the compressed plates of said cell to move toward each other to form a sheet therein which is of substantially uniform thickness and has smooth surfaces; and F removing said plates to release said sheet.

2. A method as set forth in claim 1, wherein said fluid precursor composition is an acrylic resin.

3. A method as set forth in claim 1, wherein said fluid precursor composition is an allyl diglycol carbonate.

4. A method as set forth in claim 1, wherein said fluid precursor composition is an unsaturated polyester resin.

5. A method as set forth in claim 1, wherein said fluid precursor composition is an epoxy resin.

6. A method as set forth in claim 1, wherein said fluid precursor composition is a silicone rubber.

7. A method as set forth in claim 1, wherein said fluid precursor composition is a polyurethane.

8. A method as set forth in claim 1, wherein said pretreatment involves fixation.

9. A method as set forth in claim 1, wherein said pretreatment involves dehydration.

10. A method as set forth in claim 1, wherein said pretreatment involves staining.

11. A method as set forth in claim 1, wherein said plates are of hardened glass.

12. A method as set forth in claim 11, wherein the inner surfaces of said glass are covered with foil to avoid the formation of boundary lines.

13. An examinable plastinated sheet constituted by a cut section of biological tissue impregnated with a cured polymer, the periphery of the section being surrounded by a region of cured polymer formed between two plates to define a sheet of uniform thickness which is substantially equal to that of the section in its untreated state, said sheet having smooth surfaces and being free of boundary lines between the cut section and the surrounding polymer region.

14. A sheet as set forth in claim 13, wherein said cured polymer is an acrylic resin.

15. A sheet as set forth in claim 13, wherein said cured polymer is an epoxy resin.

16. A sheet as set forth in claim 13, wherein said cured polymer is a polyester resin.

17. A sheet as set forth in claim 13, wherein said polymer is transparent.

18. A sheet as set forth in claim 13, wherein the cured polymer impregnating the tissue is of a composition that differs from that of the surrounding polymer.

19. A method as set forth in claim 1, wherein the formation of boundary lines is avoided by removing the plates to release the sheet before the precursor composition is fully cured, the curing being completed after the sheet is released.

* * * * *